(12) United States Patent
Sundararajan (10) Patent No.: US 7,850,907 B2
(45) Date of Patent: Dec. 14, 2010

(54) FABRICATING STRUCTURES IN MICRO-FLUIDIC CHANNELS BASED ON HYDRODYNAMIC FOCUSING

(75) Inventor: Narayanan Sundararajan, San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 1445 days.

(21) Appl. No.: 11/240,185

(22) Filed: Sep. 29, 2005

(65) Prior Publication Data

US 2006/0033243 A1    Feb. 16, 2006

Related U.S. Application Data

(62) Division of application No. 10/609,322, filed on Jun. 26, 2003, now Pat. No. 7,381,361.

(51) Int. Cl.
*B01L 1/00* (2006.01)
(52) U.S. Cl. .................. 422/50; 422/101; 137/807; 264/494
(58) Field of Classification Search ............. 137/807; 422/50, 101
See application file for complete search history.

(56) References Cited

U.S. PATENT DOCUMENTS

| | | | |
|---|---|---|---|
| 3,871,770 A | 3/1975 | Von Behrens et al. |
| 5,858,187 A | 1/1999 | Ramsey et al. |
| 5,972,710 A | 10/1999 | Weigl et al. |
| 6,067,157 A | 5/2000 | Altendorf |
| 6,120,666 A | 9/2000 | Jacobson et al. |
| 6,159,739 A | 12/2000 | Weigl et al. |
| 6,382,228 B1 | 5/2002 | Cabuz et al. |
| 6,408,878 B2 | 6/2002 | Unger et al. |
| 6,454,945 B1 | 9/2002 | Weigl et al. |
| 6,488,872 B1 | 12/2002 | Beebe et al. |
| 6,506,609 B1 | 1/2003 | Wada et al. |
| 2002/0182747 A1 | 12/2002 | Beebe et al. |
| 2002/0194909 A1* | 12/2002 | Hasselbrink et al. .......... 73/253 |
| 2003/0054652 A1 | 3/2003 | Mensing et al. |

(Continued)

FOREIGN PATENT DOCUMENTS

WO    WO 00/56444    9/2000

(Continued)

OTHER PUBLICATIONS

J.R. Anderson, et al., "Fabrication of Topologically Complex Three-Dimensional Microfluidic Systems in PDMS by Rapid Prototyping," *Analytical Chemistry*, vol. 72, No. 14, Jul. 15, 2000. pp. 3158-3164.

(Continued)

*Primary Examiner*—Jill Warden
*Assistant Examiner*—Timothy G Kingan
(74) *Attorney, Agent, or Firm*—Pillsbury Winthrop Shaw Pittman LLP (57) ABSTRACT

Forming a structure attached to a micro-fluidic channel based on hydrodynamic focusing is disclosed. In one aspect, a polymerizable fluid and a focusing fluid may be introduced into a hydrodynamic focusing system. The polymerizable fluid may be hydrodynamically focused with the focusing fluid. Then the focused polymerizable fluid may be polymerized to form a structure attached to a channel of the hydrodynamic focusing system.

12 Claims, 9 Drawing Sheets

U.S. PATENT DOCUMENTS

2003/0083401 A1     5/2003     Schneider et al.
2004/0069717 A1*    4/2004     Laurell et al. ............... 210/748

FOREIGN PATENT DOCUMENTS

WO        WO02072235    *   9/2002

OTHER PUBLICATIONS

D.C. Duffy, et al., "Rapid Prototyping of Microfluidic Systems in Poly(dimethylsiloxane)," *Analytical Chemistry*, vol. 70, No. 23, Dec. 1, 1998. pp. 4974-4984.

P.J.A. Kenis, et al. "Fabrication Inside Microchannels Using Fluid Flow," *Acc. Chem. Res.*, vol. 33, No. 12, 2000. pp. 841-847.

P.J.A. Kenis, et al. "Microfabrication Inside Capillaries Using Multiphase Laminar Flow Patterning." Science vol. 285, Jul. 2, 1999. pp. 83-85.

G.M. Whitesides and A.D. Stroock, "Flexible Methods for Microfluidics." Physics Today, Jun. 2001 [online]. [Retrieved on Jan. 2, 2003] Retrieved from the Internet: http://www.physicstoday.org/pt/vol-54/iss-6/p42.html. pp. 1-8.

Y. Xia, G.M. Whitesides, Soft Lithography, *Agnew. Chem. Int. Ed.* 37, 551-575 (1998).

* cited by examiner

FABRICATING STRUCTURES IN MICRO-FLUIDIC CHANNELS BASED ON HYDRODYNAMIC FOCUSING

CROSS REFERENCE TO RELATED APPLICATIONS

This application is a divisional application of U.S. Ser. No. 10/609,322 filed Jun. 26, 2003 now U.S. Pat. No. 7,381,361. The disclosure of the prior application is considered part of and is incorporated by reference in the disclosure of this application.

BACKGROUND OF THE INVENTION

1. Field of the Invention

Embodiments of the invention relate generally to micro-fluidic devices. In particular, the embodiments relate to fabricating structures in micro-fluidic devices based on hydrodynamic focusing.

2. Background Information

Various approaches to fabrication within micro-fluidic devices have been discussed in the patent literature. One example is provided in U.S. Pat. No. 6,488,872 to Beebe et al. (hereinafter referred to as the '872 patent), which is not admitted to be prior art by its inclusion in the background section.

As discussed in the abstract of the '872 patent, in part microfabricated devices and methods of manufacturing the devices are disclosed. The devices are manufactured from a substrate having microscale fluid channels, and polymerizing a polymerizable mixture in the channels to form stimuli-responsive operating components of the device. The operating components can be functional or structural components. The method of manufacture obviates the traditional assembly of microscale components to form a device because the microscale components are formed in situ on or within the device. The '872 patent also discusses using hydrodynamic focusing to continuously manufacture small diameter polymeric beads and threads.

The beads and threads do not contact the channel surfaces and are removed or emerged from the channel.

BRIEF DESCRIPTION OF THE DRAWINGS

The invention may best be understood by referring to the following description and accompanying drawings that are used to illustrate embodiments of the invention. In the drawings.

DETAILED DESCRIPTION OF THE INVENTION

In the following description, numerous specific details are set forth. However, it is understood that embodiments of the invention may be practiced without these specific details. In other instances, well-known circuits, structures and techniques have not been shown in detail in order not to obscure the understanding of this description.

Forming Structures Based on Hydrodynamic Focusing

Figure 1:
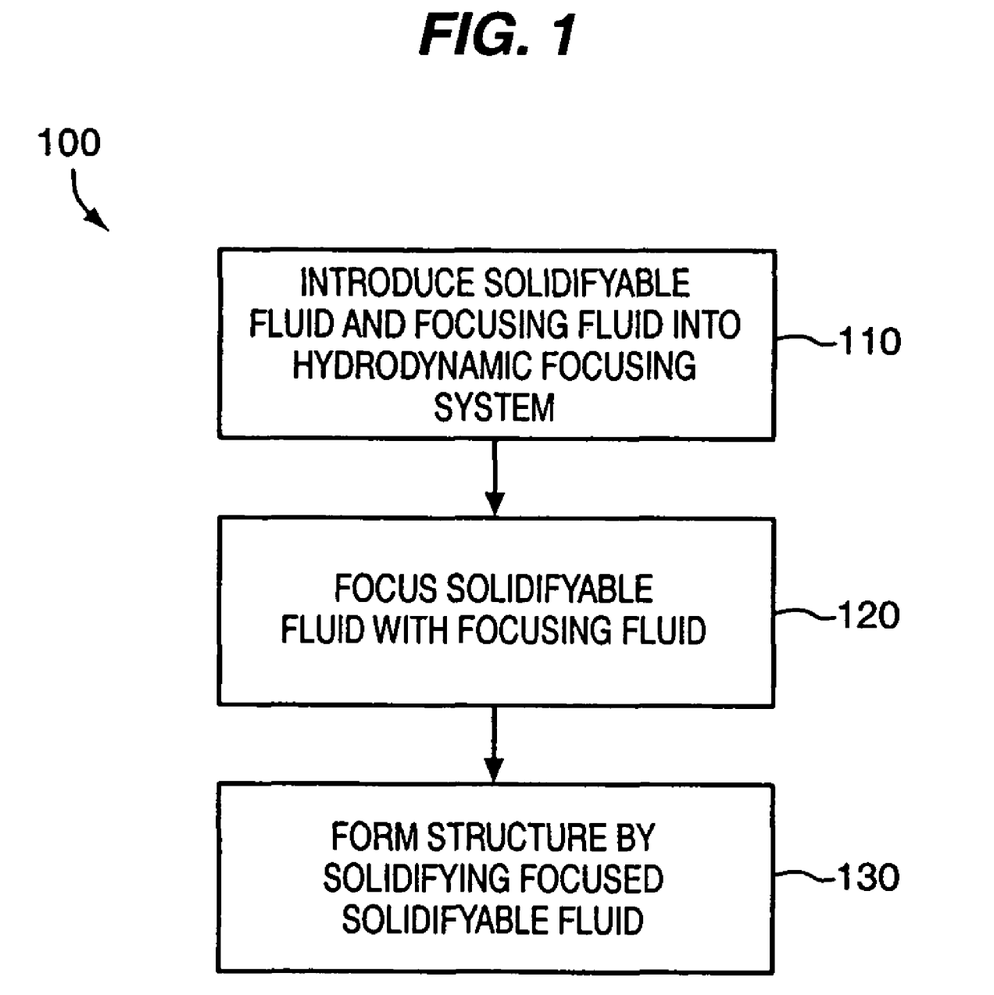
FIG. 1 shows a method for forming a structure based on hydrodynamic focusing, according to one embodiment of the invention.

FIG. 1 shows a method 100 for forming a structure based on hydrodynamic focusing, according to one embodiment of the invention. A solidifiable fluid, such as a polymerizable fluid, and a focusing fluid may be introduced into a hydrodynamic focusing system at block 110. Then, the solidifiable fluid may be hydrodynamically focused with the focusing fluid at block 120. Hydrodynamic focusing generally involves contacting a the solidifiable fluid and the focusing fluid in a focusing manifold of the hydrodynamic focusing system and focusing or otherwise reducing a cross-sectional dimension or area of one or more flows along a flow axis in the confines of the hydrodynamic focusing system.

While hydrodynamically focused, the solidifiable fluid may be polymerized or otherwise solidified to form a structure inside the hydrodynamic focusing system at block 130. In various embodiments of the invention, polymerization may be promoted by exchanging energy in the form of electromagnetic radiation or heat, with the solidifiable fluid. In one embodiment of the invention, polymerization may be selectively promoted in a portion of the focused polymerizable fluid by exposing the portion to electromagnetic radiation patterned with a lithography mask.

An exemplary structure that may be formed based on hydrodynamic focusing is a coating attached to a wall of a micro-fluidic channel. Such coatings may be employed to provide a compatible or biocompatible surface for a fluid or a component of a fluid. Another exemplary structure that may be formed based on hydrodynamic focusing is an internal divider wall. Such divider walls may be used to separate fluids on its opposite sides and perform separations, for example. Yet other exemplary structures that may be formed based on hydrodynamic focusing include but are not limited to micro-fluidic laminates, pillars, and a variety of other patterned structures.

Forming Sidewall Coatings Based on Hydrodynamic Focusing

Figure 2:
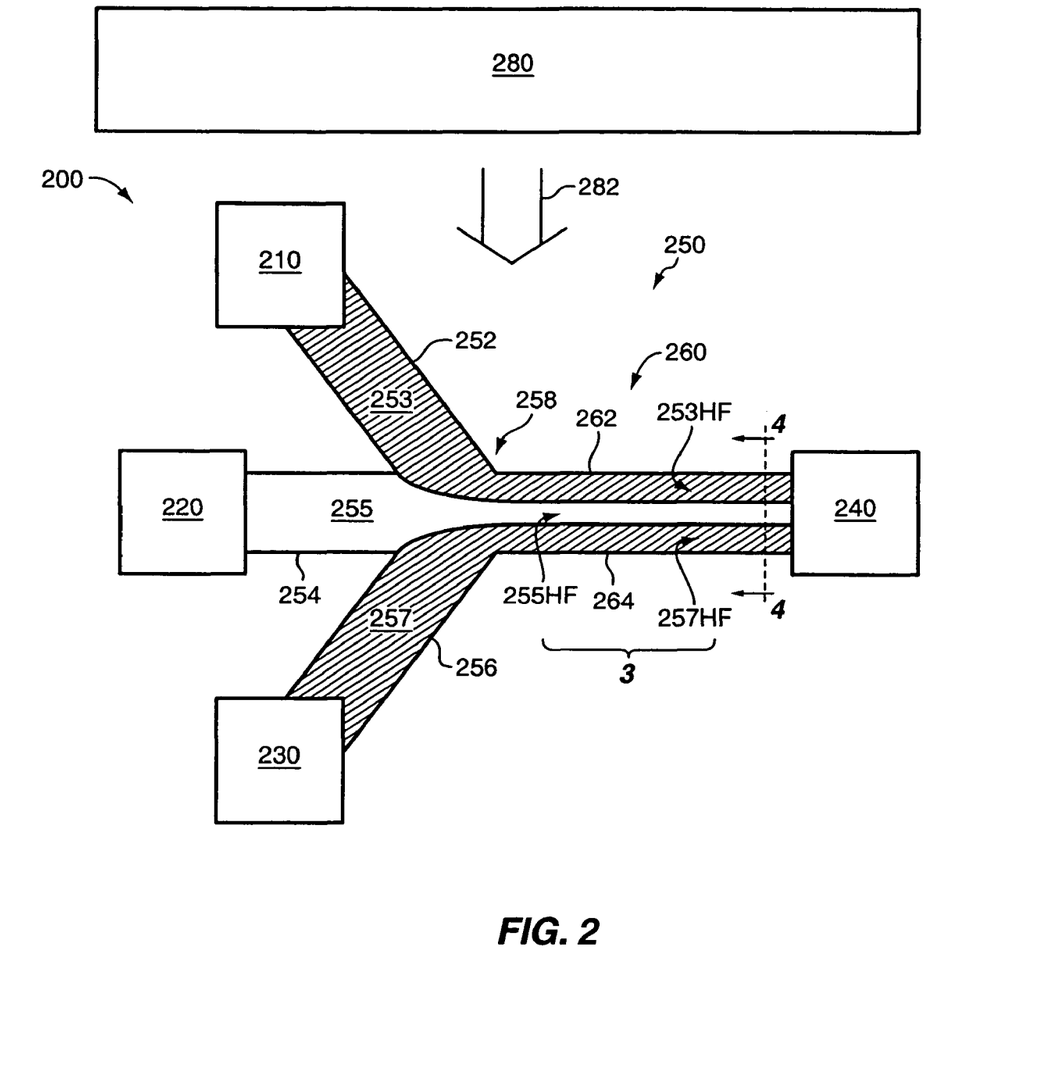
FIG. 2 shows a hydrodynamic focusing and solidification system to hydrodynamically focus and solidify fluids to form coatings attached to walls of an outlet channel of a hydrodynamic focusing system, based on an energy input from an energy input system, according to one embodiment of the invention.

FIG. 2 shows a hydrodynamic focusing and solidification system 200, according to one embodiment of the invention. The hydrodynamic focusing and solidification system 200 includes a hydrodynamic focusing system 250, a plurality of fluid sources 210, 220, 230, a fluid destination 240, and an energy input device 280. Solidifiable fluids 253, 257 and a focusing fluid 255 may be introduced into the hydrodynamic focusing system 250 from the sources 210, 220, 230. The fluids may be hydrodynamically focused within the hydrodynamic focusing system. The hydrodynamically focused solidifiable fluids 253HF, 257HF and the hydrodynamically focused focusing fluid 255HF may be conveyed through an outlet channel 260 of the hydrodynamic focusing system 250 toward the fluid destination 240. While in the outlet channel 260, the hydrodynamically focused solidifiable fluids 253HF, 257HF may be solidified to form coatings attached to vertical sidewalls walls 262, 264 of the outlet channel 260. The coatings may help to reduce a cross-sectional dimension of the outlet channel 260, separate a fluid subsequently conveyed through the outlet channel from contacting the walls 262, 264, and potentially provide a biocompatible or otherwise compatible coating for a fluid or material subsequently conveyed through the channel. When solidification is achieved by polymerization, the energy input system 280 may provide an energy input 282 to promote a more rapid polymerization.

The hydrodynamic focusing system 250 is shown in top plan view, and is coupled between the plurality of fluid sources 210, 220, 230 and the fluid destination 240. Suitable sources 210, 220, 230 for introducing the fluids include but are not limited to pumps, such as syringes or micro-fluidic pumps, and channels or chambers having sufficient pressure to promote flow. The fluids may be introduced as either steady flows or intermittent flows (for example discrete pulses). The flow rates of the fluids may be the same or different. Relatively low flow rates may be appropriate to ensure laminar flow and sufficient residence time for solidification The hydrodynamic focusing system 250 may receive the fluids from the sources 210, 220, 230. The hydrodynamic focusing system includes a first micro-fluidic inlet channel 252 coupled with a first fluid source 210 at a first end thereof, a second micro-fluidic inlet channel 254 coupled with a second fluid source 220 at a first end thereof, and a third micro-fluidic inlet channel 256 coupled with a third fluid source 230 at a first end thereof. The channels represent micro-sized fluid passages that may have a cross-sectional dimension, such as a channel width, height, or diameter, that may be less than approximately 1000 μm, 500 μm, or 100 μm. These minute dimensions promote laminar flow, which is conducive to hydrodynamic focusing. There is no known minimum or maximum length for the channels, although often the lengths are in a range between at least several times the channels widths and several centimeters. The first inlet channel 252 approaches the second inlet channel 254 from a first side thereof, at an angle, and the third inlet channel 256 approaches the second inlet channel 254 from a second, opposite, side thereof, at an angle. The illustrated angles. are each approximately 45° angles, although this is not required.

Potentially different solidifiable fluids 253, 257 may be introduced into the hydrodynamic focusing system from the first source 210 and the third source 230, respectively. Suitable solidifiable fluids include polymerizable fluids, such as epoxy resins, vinyl esters, phenolic resins, polyester resins, thermosetting resins, radiation curable resins, resists, silicones, sol-gel solutions, and others known in the arts. These fluids may contain polymerizable material, such as monomers, dimers, trimers, small polymers, crosslinking agents, or mixtures thereof, that may participate in polymerization reactions that help to solidify the fluid. The polymerizable fluid may also contain initiators, curing agents, hardeners, fillers, and other chemical additives. The use of fast-curing polymerizable fluids or crosslinkable fluids may be appropriate to allow a rapid solidification and potentially provide a three-dimensional crosslinked structure, which generally offers increased strength. Employing rapidly curing polymeric fluids may be appropriate to maintain the rate of solidification fast relative to the rate of flow to help avoid deformation due to flow. Such polymerizable fluids are commercially available from numerous sources. For example, crosslinkable EPO-TEK brand low viscosity epoxy resins are commercially available from Epoxy Technology, of Billerica, Mass.

Other potentially suitable solidifiable fluids include fluids that may be frozen within the hydrodynamic focusing system to form a structure. Generally the fluids should have a freezing point temperature that is lower than a damage threshold temperature of the hydrodynamic focusing system, and greater than an intended operating temperature of the hydrodynamic focusing system. For example, a thermoplastic, paraffin wax, or other material may be heated to above the freezing point temperature to induce melting. Then, the melted fluid may be introduced into the hydrodynamic focusing system and hydrodynamically focused. Then, the focused fluid may be cooled to below the freezing point temperature, for example by an immersion in a low-temperature liquid or other thermal quench, to induce freezing and solidification to form a structure.

Generally at about the same time as the solidifiable fluids are introduced, the focusing fluid 255 may be introduced into the hydrodynamic focusing system from the second source 220. A wide variety of focusing fluids 255 may potentially be employed. Examples include but are not limited to water, aqueous solutions, organic solvents, organic solutions, and mixtures thereof. The use of a relatively viscous fluid may be appropriate to promote laminar flow and reduce diffusion. Generally the focusing fluid should be compatible with the solidifiable fluids 253, 257, should be relatively inert, and should not solidify under the conditions used to solidify the solidifiable fluid 253, 257.

The solidifiable and focusing fluids are received from the inlet channels into a focusing manifold 258 of the hydrodynamic focusing system 250. The focusing manifold is coupled with second ends of each of the inlet channels 252, 254, 256. The focusing manifold represents a junction where the second ends of the inlet channels come together and join. The fluids may be discharged from the channels into the focusing manifold where they may be contacted and hydrodynamic focusing may be initiated. Hydrodynamic focusing generally involves contacting a plurality of flows in the focusing manifold and focusing or otherwise reducing a cross-sectional dimension or area of one or more flows along a flow axis in the confines of the hydrodynamic focusing system. In a representative example of hydrodynamic focusing, the solidifiable fluids 253, 257 and the focusing fluid 255 are contacted in the focusing manifold 258. In the laminar flow regime, which generally occurs in micro-fluidic channels and chambers, the fluids do not mix significantly, but tend to come into alignment as side-by-side co-axial flows. The laminar flow regime may be characterized by a Reynolds number that is less than approximately 2300, 1000, 100, 10, 1, 0.1, or 0.01. A small amount of mixing at interfaces between the fluids may be tolerated. At contact, the fluids may exert hydrodynamic forces or pressures on one another. Within the confines of the hydrodynamic focusing system, for example at the entrance to the outlet channel, the forces or pressures may focus or otherwise reduce cross-sectional dimensions or areas of the flows along a flow axis.

A micro-fluidic outlet channel 260 of the hydrodynamic focusing system 250 is coupled with the focusing manifold 258 at a first end thereof and with the fluid destination 240 at a second end thereof. The outlet channel 260 may receive the hydrodynamically focused solidifiable fluids 253HF, 257HF, and the hydrodynamically focused focusing fluid 255HF, from the focusing manifold 258 as side-by-side, co-axial, substantially unmixed, laminar, hydrodynamically focused flows. Lines are used to indicate approximately discrete interfaces between the fluids. A first fluid interface indicates where the first solidifiable fluid 253, 253HF contacts the focusing fluid 255, 255HF on a first side thereof. A second fluid interface indicates where the solidifiable fluid 257, 257HF contacts the focusing fluid 255, 255HF on a second opposite side thereof.

When the fluids delivered through the inlet channels have similar hydrodynamic forces, for example similar flow rates and pressures, the regions occupied by the fluids in the outlet channel tend to be similar. For example, in the illustrated embodiment, each of the fluid flows occupy approximately one-third proportion of the flow cross section of the outlet channel, as shown by the lines representing the interfaces, although this is not required. Optionally different hydrodynamic forces may be employed to allow one fluid to occupy a larger or smaller region than another fluid. Increasing the flow rate or pressure of one or more fluids generally increases the amount of focusing and decreasing the flow rate or pressure of one or more fluids generally decreases the amount of focusing.

The amount of focusing also depends upon, and tends to vary inversely with, the cross-sectional area of the outlet channel 260 available for flow. In the illustrated embodiment, the outlet channel 260 is dimensioned about the same as any one of the inlet channels (for example inlet channel 252), although this is not required. Increasing the cross-sectional area may decrease the amount of focusing and decreasing the cross-sectional area may increase the amount of focusing. By adjusting the dimensions of the outlet channel, and the flow rates and pressures of the fluids, the amount of focusing may be varied from a small amount to a large amount.

Referring again to FIG. 2, the outlet channel 260 has a first vertical sidewall 262 on a first side of the hydrodynamic focusing system (on the same side as the first inlet channel 252), and a second vertical sidewall 264 on a second, opposite, side of the hydrodynamic focusing system (on the same side as the third inlet channel 256). Terms such as "vertical," "horizontal," "upper," "lower," "ceiling," "floor," and the like, are used herein only to facilitate the description of the structure of the illustrated micro-fluidic device "as viewed." It will be evident that the devices may be used in a variety of orientations including tilted orientations. While contained within the outlet channel a first hydrodynamically focused solidifiable fluid 253HF is adjacent to and abuts the first sidewall 262. A second hydrodynamically focused solidifiable fluid 257HF is adjacent to and abuts the second sidewall 264. The focused solidifiable fluids 253HF, 257HF may occupy portions of the outlet channel adjacent to the sidewalls which span a vertical distance from a lower floor to an upper ceiling of the outlet channel. The hydrodynamically focused focusing fluid 255HF may be disposed or sandwiched between the focused solidifiable fluids 253HF and 257HF and may also occupy a portion of the outlet channel which spans a vertical distance from a lower floor to an upper ceiling. The outlet channel 260 may potentially discharge fluids to the fluid destination 240 for a period of time prior to solidification in order to establish steady or controlled flows.

The energy input device 280 is configured to input the energy 282 into at least a portion of the solidifiable fluids contained in the hydrodynamic focusing system 250. In one embodiment of the invention, the energy input device 280 may include an electromagnetic radiation source, such as a lamp or laser, to generate and transmit an electromagnetic radiation, such as light, ultraviolet (UV) light, x-rays, particle beams, electron beams, or the like, towards a radiation sensitive material in the hydrodynamic focusing system. Such radiation sources are commercially available from numerous sources, including from Advanced Radiation Corporation, of Santa Clara, Calif. The radiation may promote polymerization in the polymerizable fluid by generating free radicals, ions, or other reactive intermediates from an initiator. As one example, a photoresist may be exposed to electromagnetic radiation with a wavelength in a range between approximately 193 to 365 nm and an energy density in a range between approximately $1$ $mJ/cm^2$ to $10$ $J/cm^2$, such as may be obtained from a mercury lamp with a power in a range between approximately 100 to 350 watts. Often the curing rate increases with increasing power and energy density.

In another embodiment of the invention, the energy input device 280 may include a heat source, such as a hot plate, an oven, a heat lamp, or a resistor embedded in the housing of the hydrodynamic focusing system to input energy in the form of heat to promote polymerization in a thermosetting resin or other thermally sensitive material. In yet another embodiment of the invention, a patterned resistive heater may be formed on a surface adjacent to the outlet channel to thermally cure portions of the solidifiable fluid in the outlet channel based on a pattern of the patterned resistive heater.

The hydrodynamic focusing system 250 may receive the energy 282. In one aspect, the hydrodynamic focusing system may contain a transparent glass, quartz, sapphire, or other window, or a heat pipe of a metal or other thermally conductive material, or other dedicated inlet for the input energy 282, although this is not required. The received energy may initiate, accelerate, or otherwise promote polymerization. For example, the radiation or heat may generate free radicals, ions, or other reactive intermediates from initiators. The reactive intermediates may initiate polymerization reactions that combine monomers or other reactive material into larger molecular weight polymers. Generally the polymerization reactions rapidly increase the viscosity of the fluid. Ultimately the polymerization reactions may solidify the fluid as a non-liquid, non-flowing solid structure attached to one or more walls, or other surfaces, of the hydrodynamic focusing system. The attachment may range from a relatively weak attachment involving the solid adjacent to the wall potentially conforming to texture or roughness of the wall, to relatively more strong attachments in which the solid is chemically bonded to the wall. The solid structure need not be completely dense or hard and may be a gel or other form. In general the solid structure should have sufficient solidity to resist flowing or significantly distorting under the pressure and other forces employed in the hydrodynamic focusing system to promote flow and to maintain a shape which is at least somewhat independent of the channel.

The formed structure generally has structural features that are based on hydrodynamic focusing. Exemplary structural features include a thickness, width, or other dimension based on hydrodynamic focusing. Other exemplary structural features potentially include laminar streamlines in the form of oriented crystals, polymer chains, or other microstructure oriented with a flow direction. Yet other structural features include a boundary or interface of the structure that may be somewhat less uniform in characteristics, such as density or porosity, than a bulk of the structure, for example due to diffusion. Generally the non-uniformity may increase with distance from the focusing manifold due to increased time for diffusion.

In one embodiment of the invention, the fluids may be slowed or stopped within the hydrodynamic focusing system to allow additional residence time for solidification. The fluids may be slowed or stopped prior to or during solidification. For example, the fluids may be slowed or stopped just prior to or during the energy input. Such slowing or stopping of the fluid may be appropriate to help avoid deforming an intended shape of the structure due to flow during the solidification process. Slowing or stopping flow may also allow the use of fluids with slower solidification rates. If the flows are completely stopped in the channel the solidification may occur at a generally much slower rate that is related to diffusion instead of flow. As desired viscous fluids may be employed to additionally slow the rate of diffusion. Accordingly by slowing or stopping the flows, and by employing viscous fluids, fluids with varying solidification rates may be employed. Additionally, when the flow is slowed or stopped the shear and other forces on the flow are reduced so that a lower level of solidification may be appropriate to form a fixed structure. As desired, the formed structure may optionally be hardened by further exposure to radiation, heating, or an extended curing time.

Figure 3:
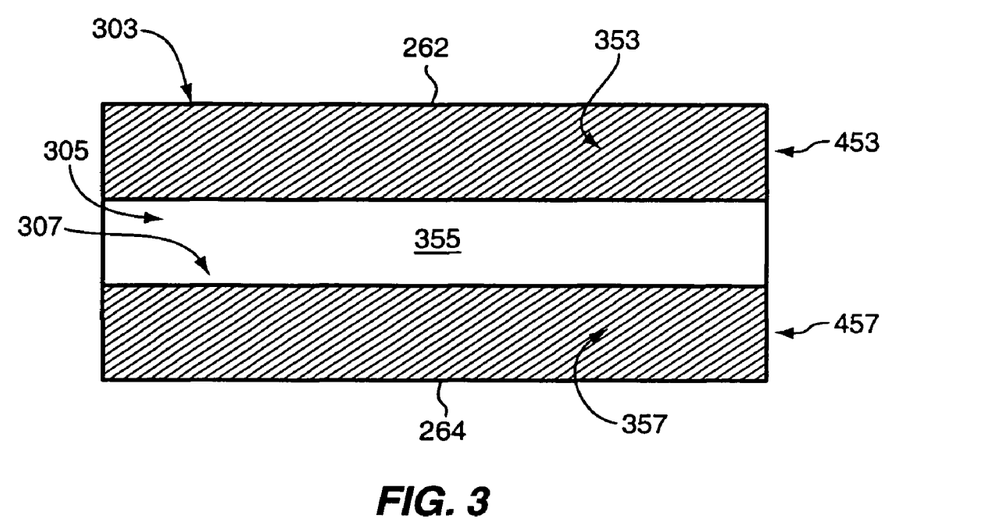
FIG. 3 shows an expanded top plan view of a portion of the outlet channel indicated by the brace 3 shown in FIG. 2.
Figure 4:
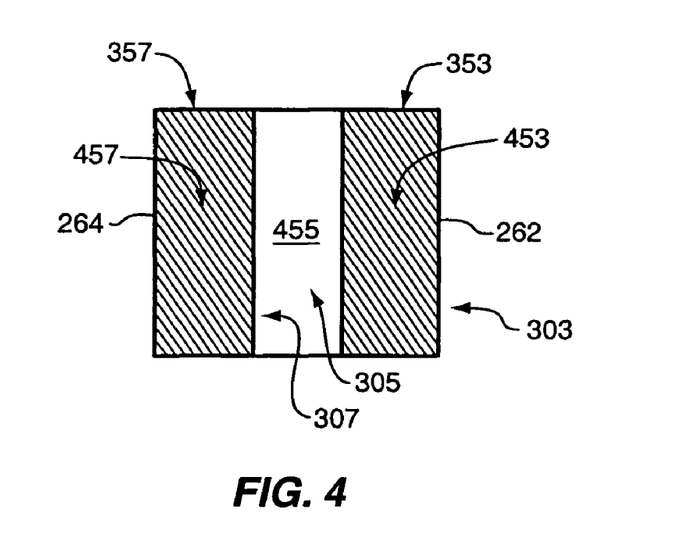
FIG. 4 shows an expanded cross-sectional view, looking down the outlet channel toward the focusing manifold, as taken along the section line 4-4 shown in FIG. 2.

FIGS. 3 and 4 show different views of an outlet channel 260 having solidified sidewall coatings 303, 307 and a micro-fluidic channel void 305 formed based on hydrodynamic focusing, according to one embodiment of the invention. The coatings 303, 305 may be formed by polymerizing or otherwise solidifying the hydrodynamically focused solidifiable fluids 253HF, 257HF. A first coating 303 is adjacent to and abuts the first vertical sidewall 262 of the outlet channel. Similarly, a second coating 307 is adjacent to and abuts the second vertical sidewall 264 of the outlet channel. The coatings may be formed in situ within the channel, may contain a polymerized or crosslinked material, and may contain a material that is different than a material of the wall. An intermediate micro-fluidic channel void 305 is disposed between a first coating 303 and a second coating 307 in the location formerly occupied by the focused focusing fluid 255HF. The focusing fluid 255HF does not polymerize or otherwise solidify under the conditions used to form the sidewall coatings and therefore may be removed from the outlet channel, for example to the fluid destination 240, to form the void 355. The void 355 represents a fluid flow path that may be used to convey fluids post formation of the coatings. The sidewall coatings and micro-fluidic channel void represent examples of structures that may be formed in a hydrodynamic focusing system, or a channel, chamber, or other portion thereof, based on hydrodynamic focusing.

FIG. 3 shows an expanded top plan view of a portion of the outlet channel indicated by the brace 3 shown in FIG. 2. A first rectangular top surface 353 of the first coating 303 is adjacent to, and in this case abutting, the first vertical sidewall 262. Similarly, a second rectangular top surface 357 of the second coating 307 is adjacent to, and in this case abutting, the second vertical sidewall 264. The top surfaces 353, 357 may be adjacent to, and in this case may abut, an upper ceiling or wall of the outlet channel 260. A rectangular void profile 355 shows that the intermediate micro-fluidic channel void 305 is disposed between the coatings 303, 307 in the outlet channel. Rightmost edges of the top surfaces 353, 357 are formed with vertical cross sectional surfaces 453, 457 shown in FIG. 4.

FIG. 4 shows an expanded cross-sectional view, looking down the outlet channel 260 toward the focusing manifold 258, as taken along the section line 4-4 shown in FIG. 2. A first vertical rectangular cross-sectional surface 453 of the first coating 303 is adjacent to, and in this case abutting, the first vertical sidewall 262. Likewise, a second vertical rectangular cross-sectional surface 457 of the second coating 307 is adjacent to, and in this case abutting, the second vertical sidewall 264. A rectangular cross-sectional void profile 455 shows that the void 305 is disposed between the coatings 303, 307 in the outlet channel. The bottom edges of the cross sectional surfaces 453, 457 may be adjacent to, and in this case abut, a lower floor or wall of the outlet channel 260. Heights of the cross sectional surfaces 453, 457, and indeed the coatings 303, 307, may span a vertical distance from the floor to the ceiling of the outlet channel 260. Topmost edges of the cross-sectional surfaces 453, 457 are formed with the top surfaces 353 and 357 shown in FIG. 3.

The coatings 303, 307 may contain a material that is different than a material of the vertical sidewalls 262, 264 and may separate a fluid conveyed through the void from contacting the sidewalls. A potential advantage is an ability to coat the sidewalls with a polymeric or other material having a characteristic that is better suited for a fluid, or a molecule or other component of the fluid, compared to a corresponding characteristic of the vertical sidewalls. For example, the coatings may have a composition, chemical compatibility, biocompatibility, smoothness, or other characteristic, that is better suited for the fluid or molecule than the vertical sidewalls. In one aspect, polytetrafluoroethylene or another chemically resistant material may be included in a coating to provide an improved chemical compatibility to a solvent (e.g., methanol), acid, or like chemical conveyed through the channel compared to a material of the sidewalls. This may be used to help protect the material of the sidewalls from corrosion or swelling, for example.

A biocompatible coating may contain a material that is more compatible relative to a biological material than a material of the vertical sidewalls. The biological material may include a biological molecule, biological particle, or biological fluid. Exemplary biological molecules include among others macromolecules, enzymes, proteins, protein derivatives, protein fragments, polypeptides, nucleic acids, DNAs, RNAs, nucleic acid derivatives, biological molecules tagged with particles, fluorescently labeled biological molecules, charged species, and charged proteins. Exemplary biological particles include among others cells, organelles, and liposomes. Exemplary biological fluids include blood, urine, and solutions of biological molecules and particles.

As is known, proteins and other biological molecules, and cells and other biological particles, may adhere to and foul glass, quartz, metals, certain polymers, and other materials that are commonly used as sidewall materials. In one aspect, a biocompatible anti-fouling coating may contain a material that is more biocompatible relative to a fouling property of a biological material than a vertical sidewall material, such as quartz. The coating may reduce a tendency of the material or molecule to adhere to, foul, or corrode, the hydrodynamic focusing system.

Exemplary biocompatible anti-fouling coatings include but are not limited to polymers containing ethylene glycol, hydroxy propyl methyl cellulose, polytetrafluoroethylene (e.g., Teflon®), or other biocompatible materials known in the arts. Other exemplary biocompatible coatings may include biocompatible epoxy resins that are commercially available from Epoxy Technology, of Billerica, Mass. As another option, biocompatible fillers, such as biocompatible nanoparticles, may be incorporated into the coating in order to increase biocompatibility of the coating. Suitable biocompatible fillers include among others polytetrafluoroethylene particles, hydroxy propyl methyl cellulose particles, and polyethylene glycol particles. Other suitable biocompatible fillers include a variety of particles coated with such biocompatible materials. After forming such a biocompatible coating, a fluid having a biological molecule or other material may be flowed in the channel adjacent to and in contact with the biocompatible coating. The biocompatible coatings may experience less adherence, fouling, or corrosion by proteins or other biological materials than would be expected for quartz or other materials used to form hydrodynamic focusing systems.

In another aspect, a biocompatible affinity coating may contain an antibody, selective biological receptor, or other binding material, to selectively adhere or bind a biological molecule, such as a protein, or other component of a fluid conveyed through the channel. Such an affinity coating may be employed in an affinity chromatography or other application to bind and help separate, purify, or test for the protein or other component of the fluid in the channel. If desired, one of the coatings may contain one binding material and another of the coatings may contain another binding material, for example by introducing the different binding materials through different inlets. Also, a plurality of different binding materials may be incorporated in a single coating by serially introducing them through a common inlet or by introducing them through a series of inlets. This may allow using a common channel to retain a plurality of different proteins or other fluid components and may potentially allow testing, separating, or purifying a multi-protein, or multi-component system in the common channel.

The thickness of the coatings 303, 307 (as shown by the widths of the first and second top surfaces 353, 357 and the widths of the first and second cross sectional surfaces 453, 457) may be based on hydrodynamic focusing. In particular, the thickness may be based on a fluid flow characteristic, such as flow rate or pressure, of one or more, of the fluids introduced into the hydrodynamic focusing system. The illustrated sidewall coatings have approximately equal thickness, although this is not required. A different pressure or flow rate may be employed in one or more of the fluids to give one of the coatings a different thickness. Likewise, the width of the void 305 (as shown by the widths of the profiles 355, 455) may be based on hydrodynamic focusing. A smaller width may be provided by employing a relatively small focusing fluid flow rate or pressure, whereas a larger width may be provided by employing a relatively larger focusing fluid flow rate or pressure. As non-limiting examples, the thickness of a coating may be in a range of approximately 10 to 90%, or 20 to 60% of the width of the outlet channel. For example, a coating in a 100 μm channel may have a thickness in a range of approximately 10 to 90 μm, or 20 to 60 μm. A wide range of thickness may be achieved based on hydrodynamic focusing. The lengths of the coatings may also be based on hydrodynamic focusing. Depending on the flow rates, and flow characteristics of the fluids such as viscosity, lengths of up to several centimeters may be achieved. Often lengths not greater than about 1 cm are employed, since diffusion may tend to increase the non-uniformity of the thickness and properties of the coatings with increasing distance from the focusing manifold.

The width of the micro-fluidic channel void 305 is less than the width of the outlet channel 260 due to the thickness of the coatings 303, 307. In one aspect, hydrodynamic focusing may be used to resize a width or other cross-sectional dimension of a channel by forming a coating on a wall of the channel. The resized dimension may be based at least in part on hydrodynamic focusing. For example, micromachining, lithography, material reforming methods (e.g., molding, stamping, etc.), or like approaches may be used to form an initial channel. Then, hydrodynamic focusing may be used to reduce a width or other cross-sectional dimension of the channel. In this way a micro-fluidic device or structure thereof may be formed with a dimension or other feature that is based at least in part on hydrodynamic focusing instead of being based solely on conventional approaches to micro-fluidic fabrication. This may allow forming a small channel without the need to employ costly lithography masks having very small feature sizes. For example, a micro-fluidic channel having a cross sectional dimension that is less than 20 μm may be formed by using a combination of a lithographic exposure with a relatively inexpensive Mylar transparency mask having a design printed with a high-resolution printer and hydrodynamic focusing. This may also allow forming a channel having a dimension that is too small to be fabricated, or too small to be economically fabricated, using a conventional micro-fluidic fabrication approach.

Forming an Internal Divider Wall Based on Hydrodynamic Focusing

Figure 5:
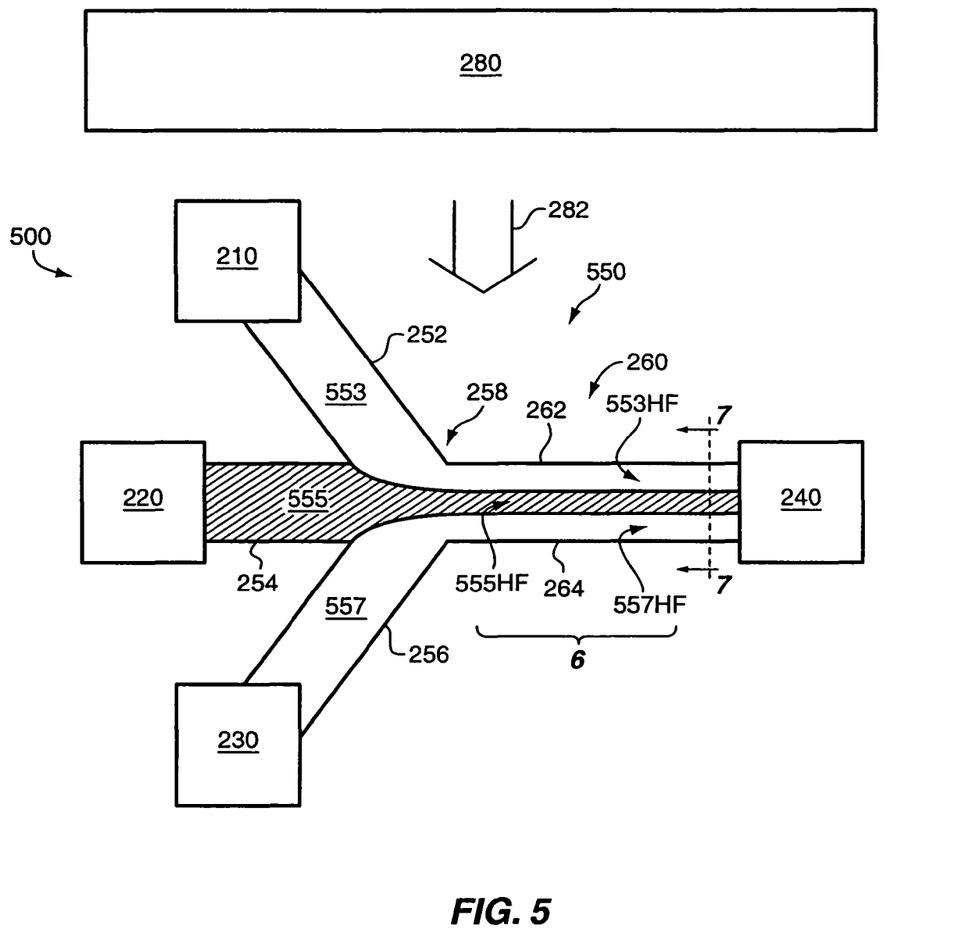
FIG. 5 shows a hydrodynamic focusing and solidification system to hydrodynamically focus a solidifiable fluid in a hydrodynamic focusing system and solidify the focused solidifiable fluid to form a divider wall in an outlet channel based on an energy input from an energy input system, according to one embodiment of the invention.

FIG. 5 shows a hydrodynamic focusing and solidification system 500 to hydrodynamically focus a solidifiable fluid 555 in a hydrodynamic focusing system 550 and solidify the hydrodynamically focused solidifiable fluid 555HF to form a divider wall in an outlet channel based on an energy input 282 from an energy input system 280, according to one embodiment of the invention. The divider wall may be used to separate fluids in micro-fluidic channel voids on opposite sides thereof and may be used as a membrane, filter, or other separator to perform a separation.

The second source 220 may introduce a solidifiable fluid 555 into the second inlet channel 254, the first source 210 may introduce a first focusing fluid 553 into the first inlet channel 252, and the third source 230 may introduce a second focusing fluid 557 into the third inlet channel 256. The focusing fluids 553 and 557 may be the same or different. The fluids 553, 555, 557 may be collected into the focusing manifold 258 where they may be contacted and hydrodynamic focusing may be initiated.

The hydrodynamically focused fluids 553HF, 555HF, 557HF exit the focusing manifold 258 through the outlet channel 260 as side-by-side hydrodynamically focused flows. Lines are used to represent approximately discrete interfaces between the fluids that are a result of the nearly unmixed laminar flow occurring in the hydrodynamic focusing system. A first fluid interface indicates where the first focusing fluid 553, 553HF contacts the solidifiable fluid 555, 555HF on a first side thereof. A second fluid interface indicates where the focusing fluid 557, 557HF contacts the solidifiable fluid 555, 555HF on a second opposite side thereof. In the illustrated embodiment, each of the flows occupy approximately one-third proportion of the flow cross section of the outlet channel, although this is not required. Other proportions may be obtained by employing a different flow rate or pressure for one or more of the fluids. The focused focusing fluids 553HF, 557HF respectively are adjacent to and abut the vertical sidewalls 262, 264. The hydrodynamically focused solidifiable fluid 555HF is intermediate in the outlet channel and disposed between the focused focusing fluids 553HF, 557HF. Each of the fluids may span a portion of the outlet channel from a lower floor to an upper ceiling.

The energy input device 280 may input energy 282, such as electromagnetic radiation, ultraviolet radiation, or heat, into the focused solidifiable fluid 555HF to promote polymerization. The solidifiable fluid, may receive the energy input. The energy 282 may promote polymerization by generating free radicals, ions, or other reactive intermediates, which may initiate polymerization reactions. Polymerization may be performed in all or any portion of the hydrodynamic focusing system, such as in the focusing manifold, inlet channels, the sources, and the destination, or a combination thereof. The polymerization reactions may solidify the solidifiable material within the hydrodynamic focusing system as a solid structure, or a semi-solid or gelatinous structure, attached to one or more surfaces or walls of the hydrodynamic focusing system. The polymerization may attach the solidifiable fluid to an upper wall or ceiling and a lower wall or floor of the outlet channel. The focusing fluids 553, 553HF, 557, 557HF are not solidified and may be removed to the fluid destination 240.

Figure 6:
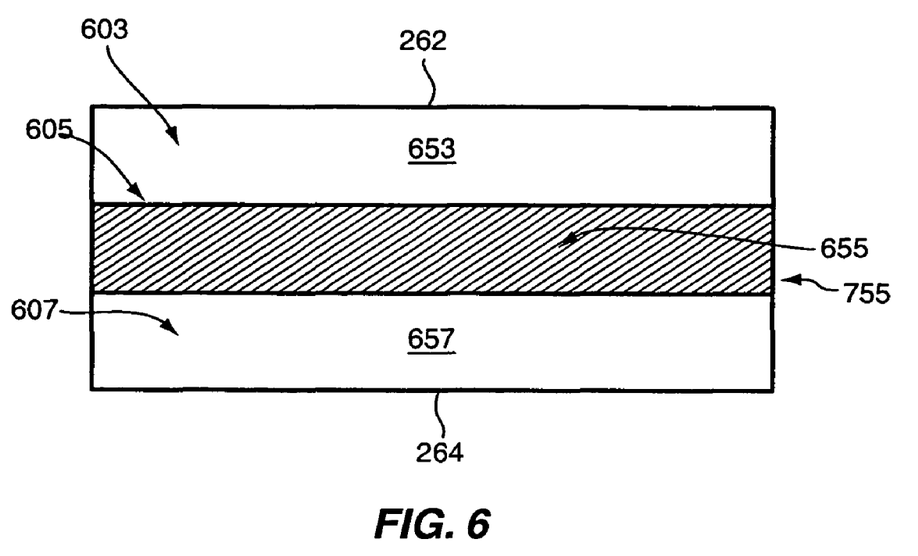
FIG. 6 shows an expanded top plan view of a portion of the outlet channel indicated by the brace 6 shown in FIG. 5.
Figure 7:
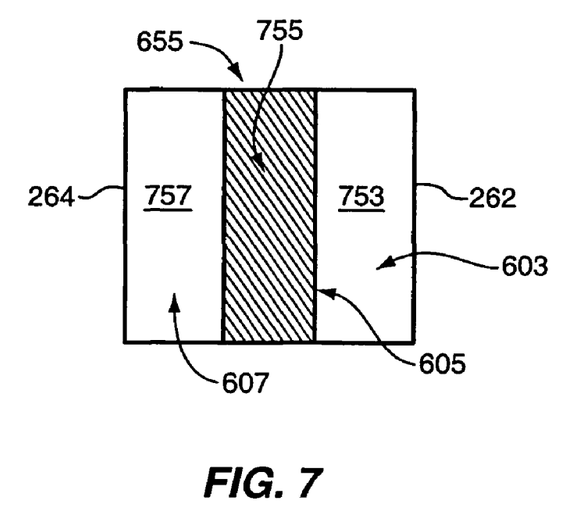
FIG. 7 shows an expanded cross-sectional view, looking down the outlet channel toward the focusing manifold, as taken along the section line 7-7 shown in FIG. 5.

FIGS. 6 and 7 show different views of an internal divider wall 605 and micro-fluidic channel voids 603, 607 formed based on hydrodynamic focusing, according to one embodiment of the invention. The divider wall 605 may be formed by polymerizing or otherwise solidifying the hydrodynamically focused solidifiable fluid 555HF in the outlet channel 260. The internal divider wall is separated from a first vertical sidewall 262 by a first micro-fluidic channel void 603 and from a second vertical sidewall 264 by a second micro-fluidic channel void 607. The internal divider wall may span a vertical distance from a top wall or ceiling to a bottom wall or floor of the outlet channel 260. The divider wall represents a structure that may be used to separate fluids on opposite sides thereof and potentially perform a separation. The channel voids 603, 607 are disposed between the divider wall 605 and the sidewalls 262, 264, respectively, in locations formerly occupied by the focused focusing fluids 553HF, 557HF. The focused focusing fluids do not solidify under the conditions used to form the divider wall and therefore may be removed from the outlet channel, for example to the fluid destination 240, to form the voids 603, 607. The channel voids represent structures that may be used to convey fluids post formation of the divider wall. The divider wall 605 and micro-fluidic channel voids 603, 607 represent examples of structures that may be formed in a hydrodynamic focusing system, or a channel, chamber, or other portion thereof, based on hydrodynamic focusing.

FIG. 6 shows an expanded top plan view of a portion of the outlet channel indicated by the brace 6 shown in FIG. 5. A rectangular top surface 655 of the internal divider wall is disposed between the voids 603, 607, and separated from the vertical sidewalls 262, 264 by the voids 603, 607. The voids are adjacent to the vertical sidewalls. The top surface 655 may be adjacent to, and in this case may abut, an upper ceiling or wall of the outlet channel 260. A first rectangular void profile 653 shows that the first micro-fluidic channel void 603 is adjacent to the first sidewall 262. Likewise, a second rectangular void profile 657 shows that the second micro-fluidic channel void 605 is adjacent to the second sidewall 264. A rightmost edge of the top surface 655 is formed with a vertical cross sectional surface 755 shown in FIG. 7.

FIG. 7 shows an expanded cross-sectional view, looking down the outlet channel 260 toward the focusing manifold 258, as taken along the section line 7-7 shown in FIG. 5. A vertical rectangular cross-sectional surface 755 of the internal divider wall is disposed between the voids 603, 607, and separated from the vertical sidewalls 262, 264 by the voids 603, 607. A first rectangular cross-sectional void profile 753 shows that the first micro-fluidic channel void 603 is adjacent to the first sidewall 262. Likewise, a second rectangular cross-sectional void profile 757 shows that the second micro-fluidic channel void 605 is adjacent to the second sidewall 264. A bottom edge of the vertical cross sectional surface 755 may be adjacent to, and in this case may abut, a lower floor or wall of the outlet channel 260. A topmost edge of the vertical cross-sectional surface 755 is formed with the top surfaces 655 shown in FIG. 6 and may be adjacent to, and abut, an upper wall or ceiling of the outlet channel 260. Accordingly, the internal divider wall may have a vertical height that spans a vertical distance from the floor to the ceiling of the outlet channel 260.

The thickness of the internal divider wall 605 (as shown by the widths of the top surface 655 and vertical cross sectional surface 755) may be based on hydrodynamic focusing. In particular, the thickness of the divider wall may be based on a flow rate or pressure of one or more of the fluids introduced into the hydrodynamic focusing system. Likewise, the widths of the voids 603, 607 (as shown by the widths of the profiles 653, 657, 753, 757) may be based on hydrodynamic focusing. The illustrated voids and the divider wall each have approximately the same cross-sectional dimensions, although this is not required. Any one or more may be given a different dimension than the others by employing a different flow rate or pressure. For example, a relatively small solidifiable fluid flow rate or pressure may be employed to form a thinner divider wall, or a relatively large flow rate or pressure may be employed to form a thicker divider wall. As non-limiting examples, the thickness of the internal dividing wall may be in a range of approximately 1 to 99%, 10 to 90%, or 20 to 60% of the width of the outlet channel. For example, a divider wall in a 100 μm channel may have a thickness in a range of approximately 1 to 99 μm, 10 to 90 μm, or 20 to 60 μm. A wide range of thickness may be achieved based on hydrodynamic focusing.

As shown, the widths of each of the two micro-fluidic channel voids 603, 607 are less than the width of the original outlet channel 260, due to the internal divider wall 605. In one aspect, very narrow channel voids 603, 607 may be formed, by forming a thick internal divider wall having a thickness approaching that of the outlet channel. As discussed above, forming such narrow channel voids may be difficult and expensive using conventional micro-fluidic device fabrication approaches, such as lithography. Hydrodynamic focusing may potentially be used to form a channel having a narrow width below that which may be fabricated, or economically fabricated, using a conventional approach, such as lithography.

As shown, the divider wall 605 may separate a first fluid conveyed through the first micro-fluidic channel void 603 from a second potentially different fluid conveyed through the second micro-fluidic channel void 607. In one aspect, the divider wall may be employed as a membrane, filter, or other separator, to filter, permeate, or otherwise separate a molecule, particle, or other species. For example, a first molecule, such as a lower molecular weight biological molecule, may be selectively permeated across the divider wall relative to a second molecule, such as a higher molecular weight biological molecule. The lower molecular weight molecule generally has a smaller size, higher diffusion coefficient, higher permeability coefficient, and may permeate the divider wall faster than the higher molecular weight molecule. Alternatively, the divider wall may be used to selectively introduce a molecule or other species. Alternatively, the divider wall may be used for other functions, such as to bind a component with a binding material of the divider wall for separation, purification, affinity chromatography, or testing, for example.

The diffusivity, permeability, porosity, or other mass transfer characteristic of the divider wall may be controlled by a variety of approaches. One approach involves using hydrodynamic focusing to tailor the thickness and the corresponding permeability of the divider wall. The permeability generally increases as the thickness decreases. Another approach involves using an amount of crosslinking agent in the polymerizable fluid to tailor the diffusivity and the permeability of the divider wall. The diffusivity and permeability generally decrease with increasing amount of crosslinking agent. Yet another approach involves incorporating dissolvable nanoparticles into the divider wall in varying proportions to tailor a porosity or permeability of the divider wall. The porosity and permeability generally increase with increasing proportion and size of the nanoparticles. Exemplary dissolvable nanoparticles include but are not limited to silver colloidal aggregates that may be dissolved with nitric acid and crystals of a salt that may be dissolved with water.

In FIGS. 2 and 5 at least one of the fluids was a non-solidifiable focusing fluid, although this is not required, and in another embodiment of the invention all of the fluids may be solidifiable fluids. For example, three different solidifiable fluids may be substituted for the fluids 253HF, 255HF, and 257HF shown in FIG. 2 to form a micro-fluidic laminate including three discrete layers of different materials in the outlet channel. In one aspect each of the layers may have a different refractive index and the laminate may be employed in an optical application.

Forming Pillars Based on Hydrodynamic Focusing and Patterning

Figure 8:
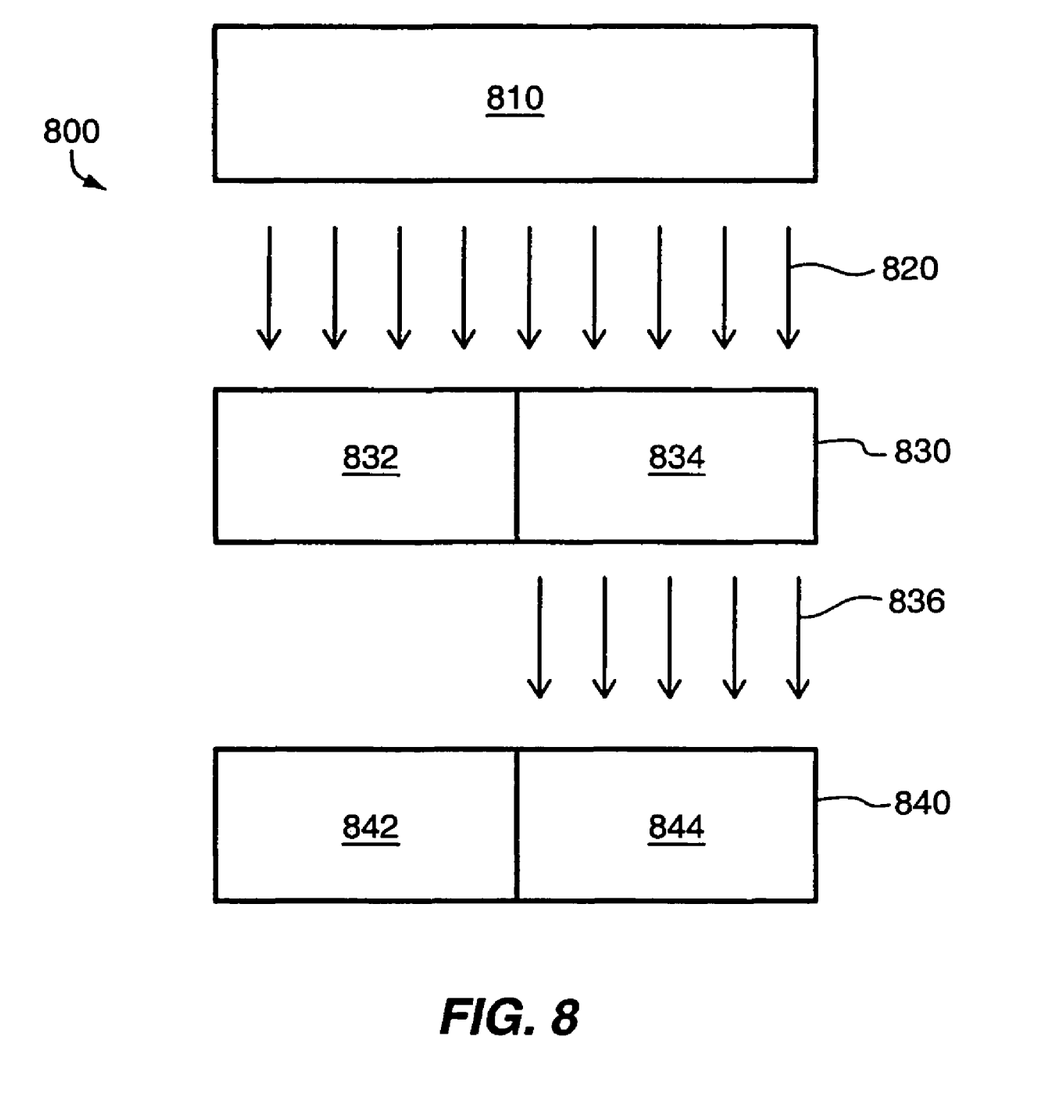
FIG. 8 shows a lithography system for forming a lithographically patterned structure from a hydrodynamically focused radiation sensitive fluid, according to one embodiment of the invention.

FIG. 8 shows a lithography system 800 for forming a lithographically patterned structure from a hydrodynamically focused radiation sensitive fluid, according to one embodiment of the invention. An electromagnetic radiation source 810 may generate and transmit an electromagnetic radiation 820, such as light, ultraviolet light, x-rays, particle beams, electron beams, or the like, towards a hydrodynamic focusing system 840, through a patterned mask 830. The patterned mask 830 may represent a device comprising a functional pattern that acts as a selective barrier to the passage of electromagnetic radiation. The patterned mask 830 may have a transparent region that selectively transmits a portion 836 of the radiation 820 and an opaque region that selectively blocks another portion. The patterned mask may include alternating regions of opaque chrome on transparent quarts, or other transparent and opaque materials may be employed. In any event, the patterned mask 830 may selectively allow a portion 836 of the incident electromagnet radiation 820 to pass on to the hydrodynamic focusing system 840.

The hydrodynamic focusing system 840 may contain a radiation sensitive material. Suitable radiation sensitive materials include epoxy resins and other polymerizable fluids mentioned above. These radiation sensitive fluids may be chemically and physically transformed and solidified based on an exposure to electromagnetic radiation. The hydrodynamic focusing system may receive the portion 836 of the electromagnetic radiation that is transmitted by the patterned mask 830. A select portion 844 of radiation sensitive material contained within the hydrodynamic focusing system 840 may be exposed and polymerization selectively promoted therein. The exposed portion 844 may be solidified as a structure in the hydrodynamic focusing system based on the received radiation 836. The structure may have a first dimension that is based on hydrodynamic focusing and a second dimension that is based on the patterned mask. Another portion 842 may not be exposed, transformed, or solidified due to selective patterning of the radiation 820 by the patterned mask 830.

Figure 9:
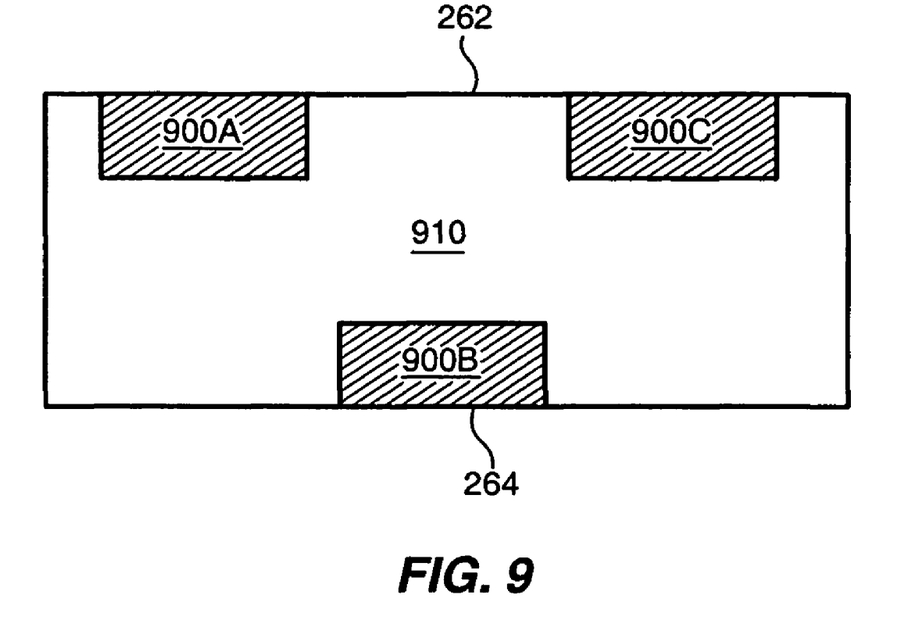
FIG. 9 shows a top plan view of a portion of an outlet channel having a plurality of pillars attached to outlet channel sidewalls and formed based on a combination of hydrodynamic focusing and lithographic patterning, according to one embodiment of the invention.

FIG. 9 shows a top plan view of a portion of an outlet channel having a plurality of pillars 900A-C attached to outlet channel sidewalls 262, 264 and formed based on a combination of hydrodynamic focusing and lithography, according to one embodiment of the invention. The illustrated pillars include a first pillar 900A and a third pillar 900C attached to a first sidewall 262 and a second pillar 900B attached to a second sidewall 964. The illustrated pillars have rectangular top surfaces, although square, circular, oval, or other top surface shapes may optionally be employed. Different numbers, configurations, and shapes of pillars may also optionally be employed. The pillars may be formed by using a mask to selectively expose portions of hydrodynamically focused solidifiable fluid adjacent to the walls, as shown in FIG. 2, that correspond in position and volume to the pillars. A first dimension of the pillars, such as a width, may be based on hydrodynamic focusing. A second dimension of the pillars, such as a length, may be based on lithography. The height of the pillars may span the distance from the floor to the ceiling of the outlet channel.

Figure 10:
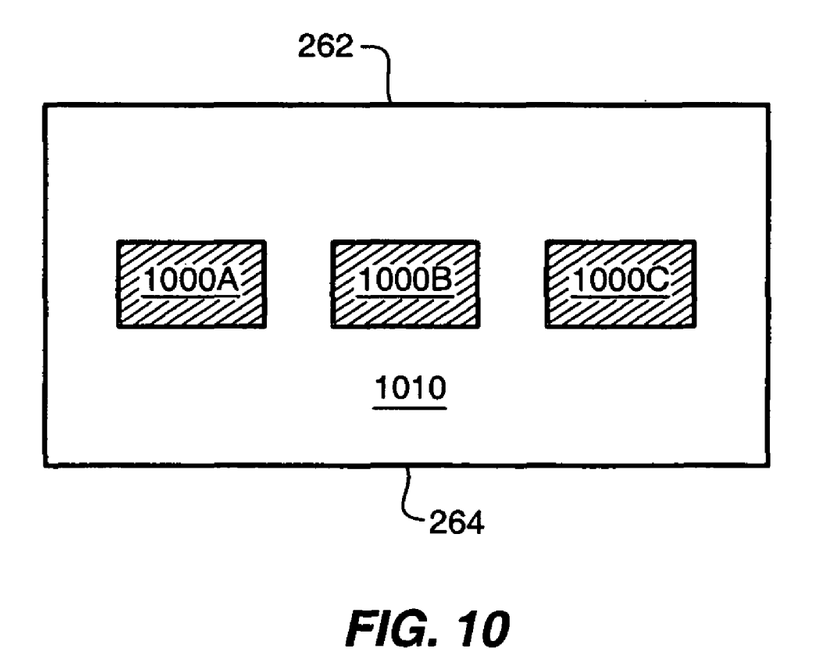
FIG. 10 shows a top plan view of a portion of an outlet channel having a plurality of internal pillars which are disposed between and separated from vertical sidewalls and formed based on hydrodynamic focusing and lithographic patterning, according to one embodiment of the invention.

FIG. 10 shows a top plan view of a portion of an outlet channel having a plurality of internal pillars 1000A-C which are disposed between and separated from vertical sidewalls 262, 264 and are formed based on lithographic patterning and hydrodynamic focusing, according to one embodiment of the invention. The illustrated pillars include a first pillar 900A and a third pillar 900C attached to a first sidewall 262 and a second pillar 900B attached to a second sidewall 964. Different numbers, configurations, and shapes of pillars may also optionally be employed. The pillars may be formed by using a mask to selectively expose portions of hydrodynamically focused solidifiable fluid intermediate between focusing fluids, as shown in FIG. 5, that correspond in position and volume to the pillars. A first dimension of the pillars, such as a width, may be based on hydrodynamic focusing. A second dimension of the pillars, such as a length, may be based on lithography. The height of the pillars may span the distance from the floor to the ceiling of the outlet channel and the pillars may be attached to the floor and the ceiling.

The pillars shown in FIGS. 9 and 10 may be used for a variety of purposes. One potential use is as a flow around structure to divert or modify flow, or perform fluid mixing. Another potential use is as extra surface area for catalysis, ion exchange, sorption (for example adsorption or absorption), component binding, protein binding, affinity chromatography, or other surface area dependent processes. Yet another potential use is as a pillar containing a material that can be controllably expanded and contracted with temperature, pH, or other activator to form a valve or other flow control device. The pillars may also be grouped together and with conventional structures, to form gates, valves, pumps, and other micro-fluidic devices.

Other Hydrodynamic Focusing Systems

Figure 11:
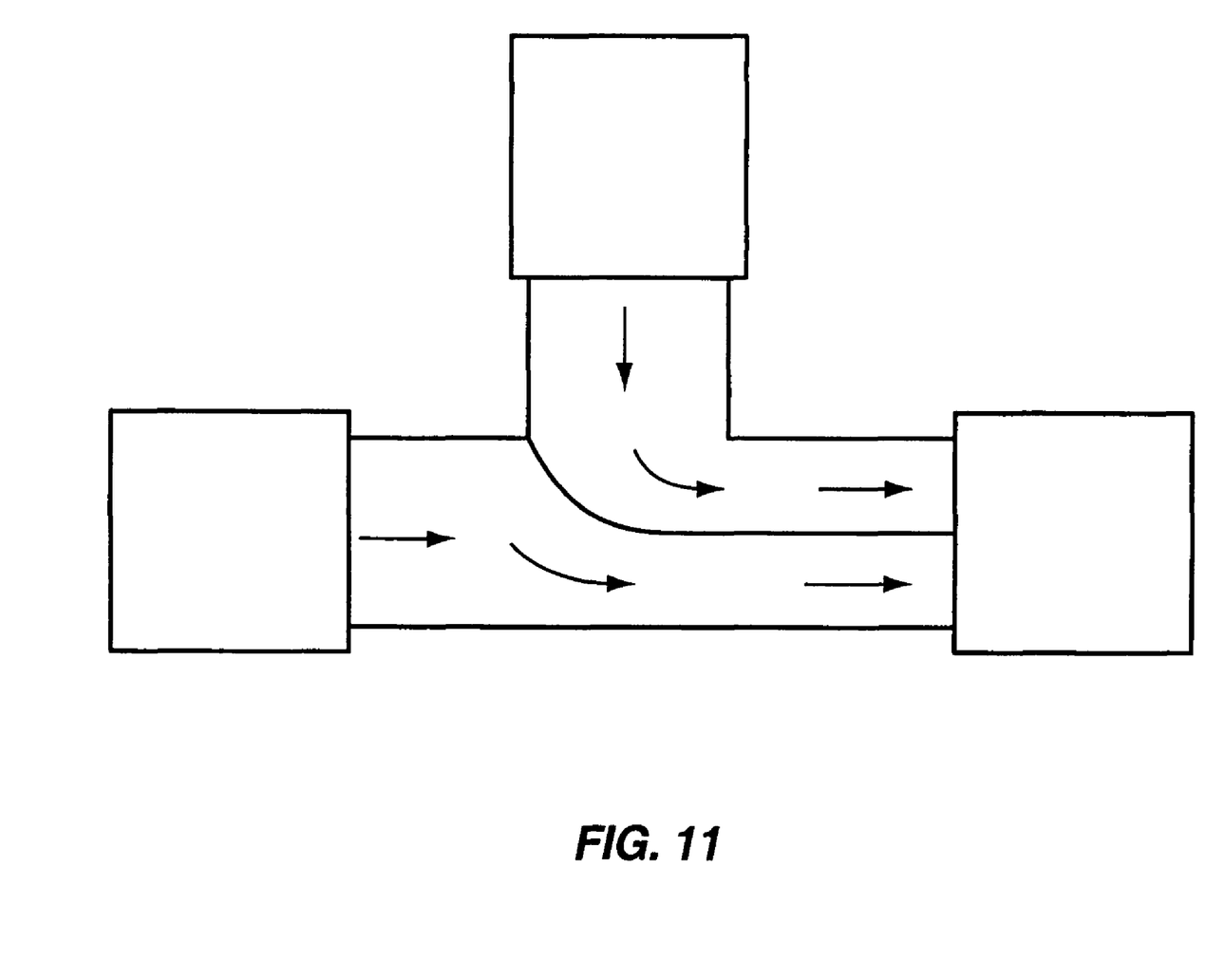
FIG. 11 shows a top plan view of another hydrodynamic focusing system in which an embodiment of the invention may be implemented.
Figure 12:
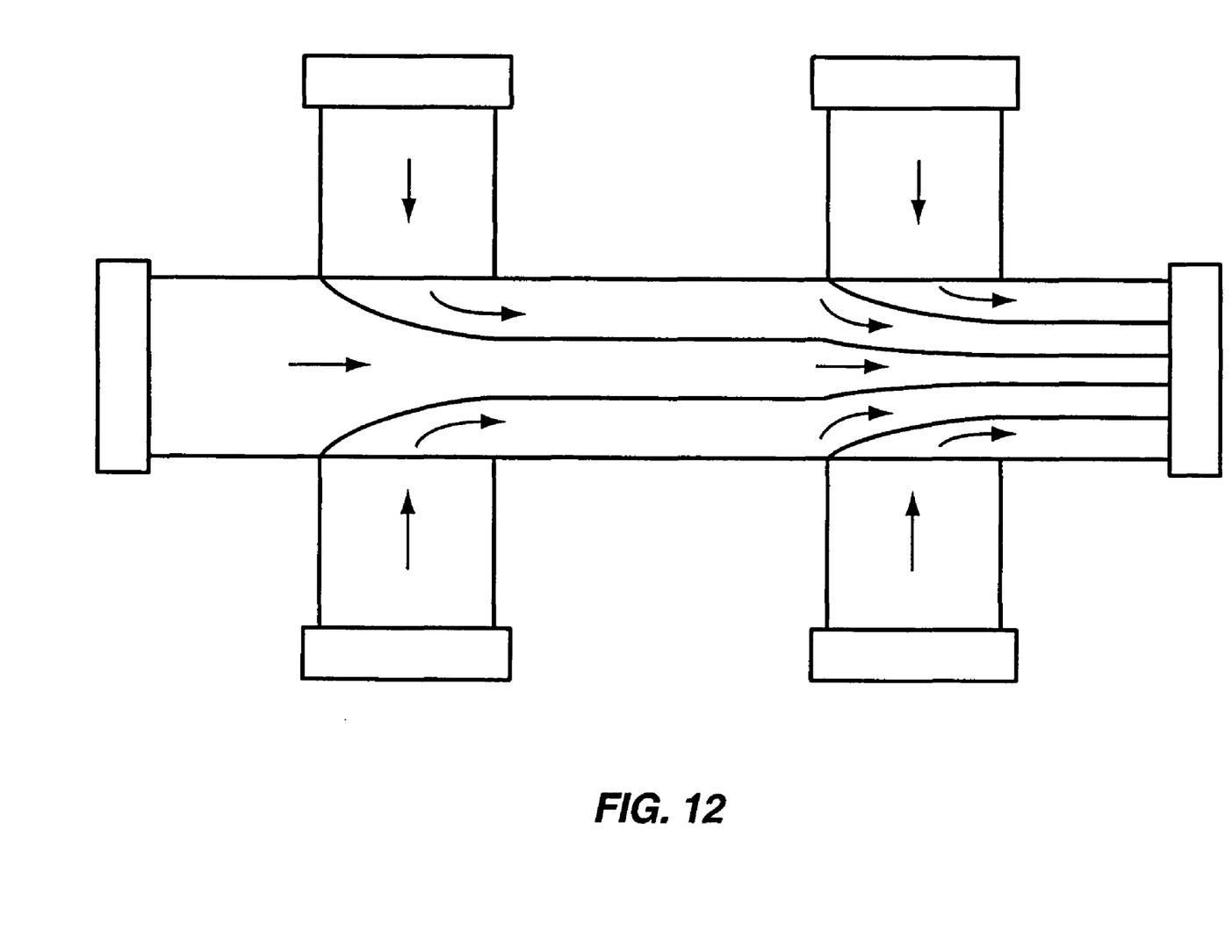
FIG. 12 shows a top plan view of yet another hydrodynamic focusing system in which an embodiment of the invention may be implemented with recursive hydrodynamic focusing.

Concepts have been illustrated with the use of a particular hydrodynamic focusing system, although those having an ordinary level of skill in the art, and the benefit of the present disclosure, will appreciate that embodiments of the invention may be practiced with a wide variety of hydrodynamic focusing systems. For example, an embodiment of the invention may be practiced with the hydrodynamic focusing system shown in FIG. 11. As another example, various embodiments of the invention may be practiced with the hydrodynamic focusing systems discussed in U.S. Pat. Nos. 5,858,187, 6,120,666, 6,159,739, and U.S. Pat. No. 6,506,609. As yet another example, an embodiment of the invention may be practiced with recursive hydrodynamic focusing using the hydrodynamic focusing system shown in FIG. 12, which includes a plurality of focusing manifolds in series. As a further example, an embodiment of the invention may be practiced with one of the hydrodynamic focusing systems disclosed in co-pending U.S. patent application Ser. No. 10/609,227, entitled "HYDRODYNAMIC FOCUSING DEVICES", filed on Jun. 26, 2003, by Sundararajan et al. These hydrodynamic focusing systems may allow forming a coating, pillars, or other structures on all walls of an outlet channel, forming a tilted structure, or allow greater control over the shape and positioning of a formed structure.

General Matters

In the description above, for the purposes of explanation, numerous specific details are set forth in order to provide a thorough understanding of the present invention. It will be apparent, however, to one skilled in the art that the present invention is not limited to the embodiments described, but can be practiced without some of these specific details, and can be practiced with modification and alteration within the spirit and scope of the appended claims. In other instances, well-known structures, devices, and techniques have been shown in block diagram form or without detail in order not to obscure the understanding of this description. With respect to the above description then, it is to be realized that the optimum dimensional relationships for the parts of the invention, to include variations in size, materials, shape, form, function and manner of operation, assembly and use, are deemed readily apparent to one of ordinary skill in the art, and all equivalent relationships to those illustrated in the drawings and described in the specification are intended to be encompassed by embodiments of the present invention.

Many of the methods are described in their most basic form, but operations can be added to or deleted from any of the methods. It will be apparent to those skilled in the art that many further modifications and adaptations can be made. The particular embodiments are not provided to limit the invention but to illustrate it. The scope of the present invention is not to be determined by the specific examples provided above but only by the claims below.

It should also be appreciated that reference throughout this specification to "one embodiment" or "an embodiment" means that a particular feature can be included in the practice of the invention. Similarly, it should be appreciated that in the foregoing description of exemplary embodiments of the invention, various features of the invention are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

What is claimed is:

1. A device comprising a structure attached to a micro-fluidic channel, wherein the structure comprises a solidified, ultraviolet polymerized and hydrodynamically focused material inside the micro-fluidic channel,
   wherein the structure comprises an interior divider wall within the micro-fluidic channel, wherein the interior divider wall creates separate fluid flow channels on opposite sides of the interior divider wall to permit separate fluid flows in the separate fluid flow channels.

2. The device of claim 1, wherein the device comprises a plurality of interior divider walls.

3. The device of claim 1, wherein the structure has a dimension that is based on hydrodynamic focusing.

4. The device of claim 3, wherein the dimension is based on a flow rate of a hydrodynamically focused fluid.

5. The device of claim 3, wherein the structure comprises a plurality of coatings attached to walls of the channel.

6. The device of claim 5, wherein the coatings comprise a material having a greater biocompatibility relative to a biological molecule compared to a material of a wall of the channel.

7. The device of claim 3, wherein the structure comprises a membrane or filter.

8. The device of claim 3, wherein the structure comprises a structure having a first dimension that is based on hydrodynamically focusing on a second dimension that is based on a patterned mask.

9. The device of claim 8, wherein the structure comprises a pillar having a width that is based on hydrodynamic focusing and a length that is based on the patterned mask.

10. The device of claim 3, wherein the structure comprises a material that is different from a material of a wall of the micro-fluidic channel.

11. The device of claim 3, wherein the device comprises a plurality of interior divider structures.

12. The device of claim 1, wherein the solidified, ultraviolet polymerized and hydrodynamically focused material comprises a solid structure, a semi-solid or gelatinous structure.

* * * * *